(12) United States Patent
Edgren et al.

(10) Patent No.: US 6,210,712 B1
(45) Date of Patent: Apr. 3, 2001

(54) DOSAGE FORM HAVING FIRST AND SECOND COATS

(75) Inventors: David E. Edgren, El Granada; Robert R. Skluzacek, Newark, both of CA (US)

(73) Assignee: Alza Corporation, Mountain View, CA (US)

(*) Notice: Subject to any disclaimer, the term of this patent is extended or adjusted under 35 U.S.C. 154(b) by 0 days.

(21) Appl. No.: 09/206,211

(22) Filed: Dec. 4, 1998

Related U.S. Application Data
(60) Provisional application No. 60/067,669, filed on Dec. 5, 1997.

(51) Int. Cl.[7] ............... A61K 9/24; A61K 9/36; A61K 9/32

(52) U.S. Cl. ............ 424/473; 424/472; 424/480; 424/482

(58) Field of Search ................ 424/473, 472; 604/892

(56) References Cited

U.S. PATENT DOCUMENTS

| | | |
|---|---|---|
| 2,799,241 | 7/1957 | Wurster et al. . |
| 3,133,132 | 5/1964 | Loeb et al. . |
| 3,173,876 | 3/1965 | Zobrist et al. . |
| 3,276,586 | 10/1966 | Rosaen . |
| 3,541,005 | 11/1970 | Strathmana et al. .......... 210/19 |
| 3,541,006 | 11/1970 | Bixler et al. ................. 210/23 |
| 3,546,876 | 12/1970 | Fokker et al. . |
| 3,845,770 | 11/1974 | Theeuwes et al. .......... 128/260 |
| 3,916,899 | 11/1975 | Theeuwes et al. .......... 128/260 |
| 4,063,064 | 12/1977 | Saunders et al. ........... 219/121 |
| 4,088,864 | 5/1978 | Theeuwes et al. .......... 219/121 |
| 4,160,020 | 7/1979 | Ayer et al. .................... 424/15 |
| 4,200,098 | 4/1980 | Ayer et al. .................. 128/260 |
| 4,285,987 | 8/1981 | Ayer et al. ...................... 427/3 |
| 4,327,725 | 5/1982 | Cortese et al. ............. 128/260 |
| 4,449,983 | * 5/1984 | Cortese et al. ............. 604/892 |
| 4,612,008 | 9/1986 | Wong et al. ................. 604/892 |
| 4,783,337 | 11/1988 | Wong et al. ................. 424/468 |
| 4,863,456 | 9/1989 | Stephens et al. ............ 604/892 |
| 4,902,514 | 2/1990 | Barclay et al. .............. 424/473 |
| 5,840,329 | * 11/1998 | Bai .............................. 424/458 |

OTHER PUBLICATIONS

Roff, et al., Handbook of Common Polymers, pp. 164–173 (1971), published by CRC Press.

J. Am. Pharm. Assoc., vol. 48, pp. 451–454, (1959); and ibid., vol. 49, pp. 82–84 (1960).

Modern Plastics Encyclopedia, vol. 46, pp. 62–70 (1969).

Pharmaceutical Sciences, by Remington, 14th Ed., pp. 1626–1680 (1970), published by Mack Publishing Co.

* cited by examiner

Primary Examiner—Thurman K. Page
Assistant Examiner—Blessing Fubara
(74) Attorney, Agent, or Firm—Paul B. Simboli; Steven F. Stone; Paul L. Sabatine

(57) ABSTRACT

A dosage form comprising a composition comprising a drug surrounded by a first coat and a second coat with an exit for administering the drug to a patient; and a method of using the dosage form are disclosed for an indicated therapy.

13 Claims, 2 Drawing Sheets

DOSAGE FORM HAVING FIRST AND SECOND COATS

This application claims the priority of provisional application Ser. No. 60/067,669 filed on Dec. 5, 1997.

FIELD OF THE INVENTION

This invention pertains to a novel and to an useful dosage form that provides a long duration and linear drug release with time administered to provide a therapeutic benefit. The invention relates, more particularly, to a dosage form comprising a first coat that provides both protection to a formulation comprising a drug and increases the fluid-transmission rate into the dosage form to maintain the linear drug release over time, and to a second and different coat that provides protection to the dosage form in a biological environment of use. The invention concerns further the manufacture of the dosage form comprising the first coat and the second coat using a single solvent system in both coat manufacture.

BACKGROUND OF THE INVENTION

Pharmacy and medicine have discovered the use of dosage forms are increasingly important in the administration of drugs for better health. The dosage forms often provide improved patient compliance accompanied by better control of drug blood levels, reliable and reproducible drug-release profiles, and frequently a reduced coat of therapy.

In the past however, serious short comings were associated with the administration of drugs. For example, the dosage form did not mask an unpleasant taste, or the dosage form did not improve the stability of a drug formulation, or the dosage form did not prevent oxidation of a drug. Then too, materials used to manufacture a coat that enveloped a drug in a dosage form can abstract from the dosage form. For example, coatings made from carbohydrates are water-soluble, they readily disintegrate and give rise to noncontrolled dose dumping of a drug, or a coating made from an enteric phthalate pass intact through the stomach but undergo disintegration in the intestinal tract, or alkylcellulosic polymers such as ethylcellulose exposed to the gastrointestinal tract are lipophilic and absorb endogenous fats and consequently evidence a lack of structural integrity as seen in flaws or cracks in the coat; also, they can become impermeable to aqueous fluids including water and biological fluids to the extent they become nonfunctional for membrane-controlled delivery mechanisms.

It is clear from the above presentation that a long-felt need exists for a dosage form comprising a coat thereon for orally administering a drug at a controlled and sustained-release drug delivery profile with time. The need exists for a dosage form for administering a drug in a linear profile for cardiovascular, arthritic, respiratory, cancer, analgesic and other therapies. A dosage form is needed for replacing immediate-release dose-dumping form administered three or four times daily. There are reasons for seeking a dosage form that replaces immediate-release forms including a means for reducing peak blood levels followed by a sharp drop in blood levels, a means for lessening side effects, a means for maintaining the structural integrity of the dosage form, and a means for reducing the number of solvents to manufacture the dosage form.

OBJECTS OF THE INVENTION

Accordingly, in view of the above presentation, it is an immediate object of this invention to provide a novel and useful dosage form that overcomes the disadvantages associated with the prior art.

Another object of the present invention is to provide a dosage form comprising a first coat and a second coat that provides protection for the first coat from the environment of the gastrointestinal tract.

Another object of the invention is to provide a dosage form comprising a bilayer coat that maintains its integrity in the environment of use.

Another object of the present invention is to provide a dosage form manufactured as an osmotic drug delivery device that can be manufactured by standard manufacturing techniques into sizes, shapes, and forms that comprise an improvement in the drug dispensing art.

Another object of the invention is to make available to the drug dispensing art a dosage form comprising a bioprotective coat for protecting the dosage form in a biological environment of use.

Another object of the invention is to provide a dosage form comprising a coat comprising a blend of an ethylcellulose and a hydroxyalkylcellulose useful for manufacturing a dosage form.

Another object of the invention is to provide a dosage form comprising a first or interior coat consisting of ethylcellulose and hydroxypropylcellulose shielded by a second or exterior coat consisting of poly(cellulose acylate) from the environment of the gastrointestinal tract.

Another object of the invention is to provide a polymer composition comprising a hydrophobic polymer insoluble in the digestive system and a hydrophilic polymer soluble in the digestive system that dissolves from the composition thereby increasing the porosity and increasing the permeability of the composition.

Another object of the invention is to provide a dosage form comprising a seamless coat that surrounds a formulation of drug and a seamless-bioprotective coat that surrounds former coat, which dual coats avoid a break-up in the gastrointestinal tract while correspondingly keeping the structural integrity of the dosage form.

Another object of the invention is to provide a dosage form comprising a dual coat for the controlled delivery of drug at a predetermined rate per hour over an extended time.

Other objects, features, aspects, and advantages of the invention will be more apparent to those versed in the dispensing art from the following detailed specification taken in conjunction with the drawing figures and the accompanying claims.

BRIEF DESCRIPTION OF DRAWINGS

In the drawing figures, which are not drawn to scale, but set-forth to illustrate various manufactures of the invention, the drawing figures are presented herebelow.

Drawing

Drawing

Drawing

In the drawing figures, and in the specification, like parts and like ingredients, are identified by like numbers. The terms appearing earlier in the specification, and in the description of the drawing figures, as well as embodiments thereof, are further described in the specification.

DETAILED DESCRIPTION OF THE DRAWINGS

Figure 1:
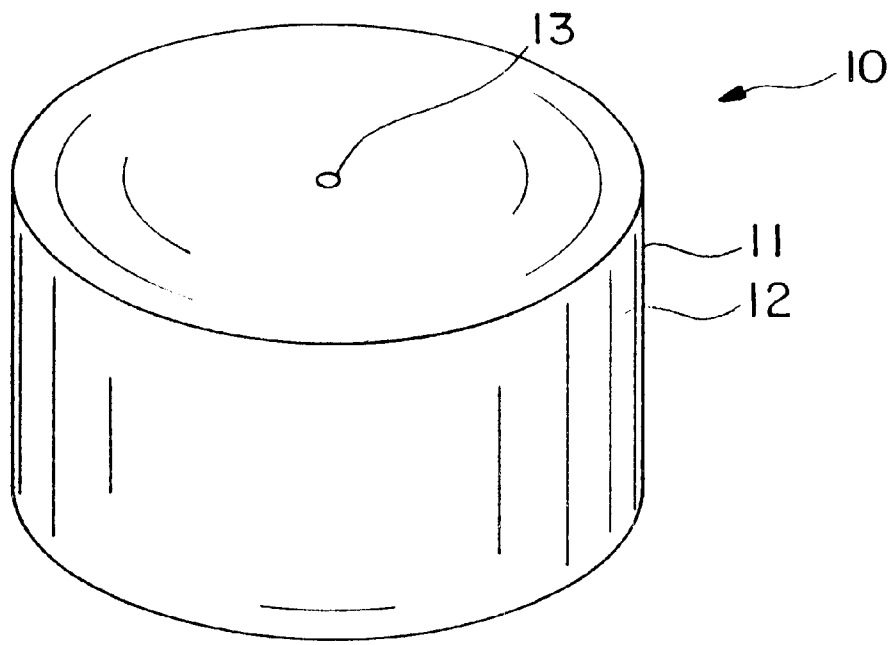
FIG. 1, is a general view of a dosage form provided by this invention designed, shaped and adapted for the oral administration of a drug at a controlled rate over an extended time to a human in need of drug therapy.

Turning attention now to the drawing figures in detail, which drawing figures are examples of a dosage form and drug composition provided by this invention, and which examples are not to be construed as limiting the invention, one example of a dosage form is seen in drawing FIG. 1. In drawing FIG. 1, a dosage form 10 is seen comprising a body member 11 that comprises an exterior or second coat 12. The exterior or second coat 12 surrounds an interior or first coat and a compartment, not seen in drawing FIG. 1. Dosage form 10 comprises at least one exit 13 that connect the exterior environment, such as the gastrointestinal tract of a human patient, with the interior of the dosage form.

Figure 2:
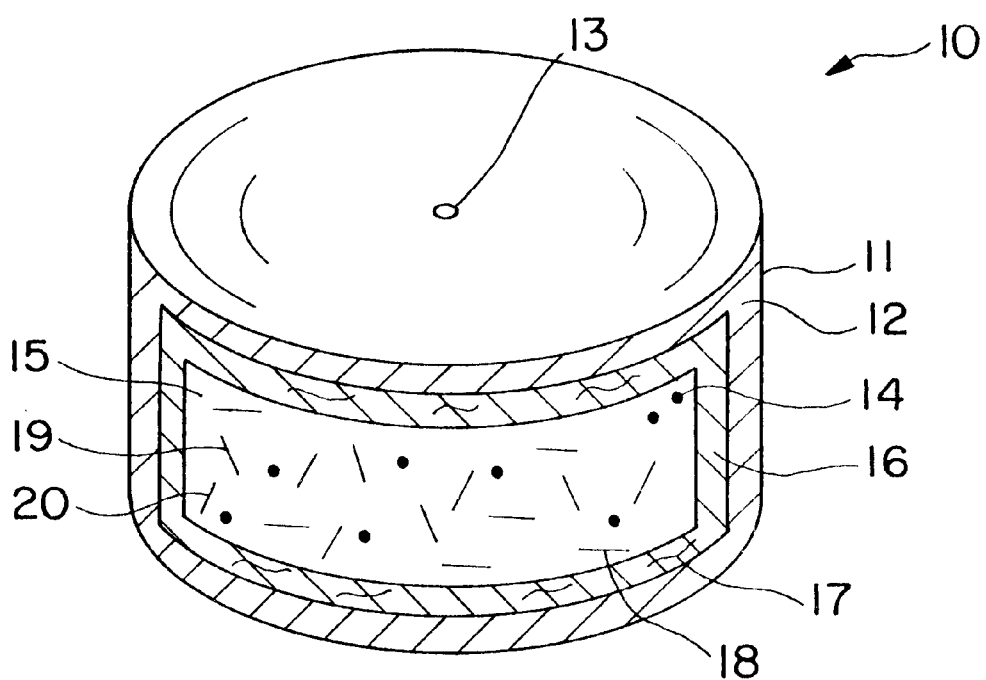
FIG. 2, is a general view of the dosage form of drawing FIG. 1, in opened section, depicting a dosage form of this invention comprising an internally housed, pharmaceutically-acceptable therapeutic drug composition.

Dosage form 10, of drawing FIG. 2, illustrates a dosage form that possesses controlled-release delivery kinetics. The dosage form delivers a drug, or a drug and its pharmaceutically-acceptable salt to a patient in need of drug therapy. The phrase, controlled-release denotes the dosage form provides a linear drug release with time, or a zero order delivery of drug. Dosage form 10 controls or governs the delivery of drug 14, represented by dots 14, from an internal space or compartment 15. Dosage form 10 delivers drug 14 at a measured rate per unit time over an extended or sustained-release time of eight hours to twenty-four hours.

Figure 3:
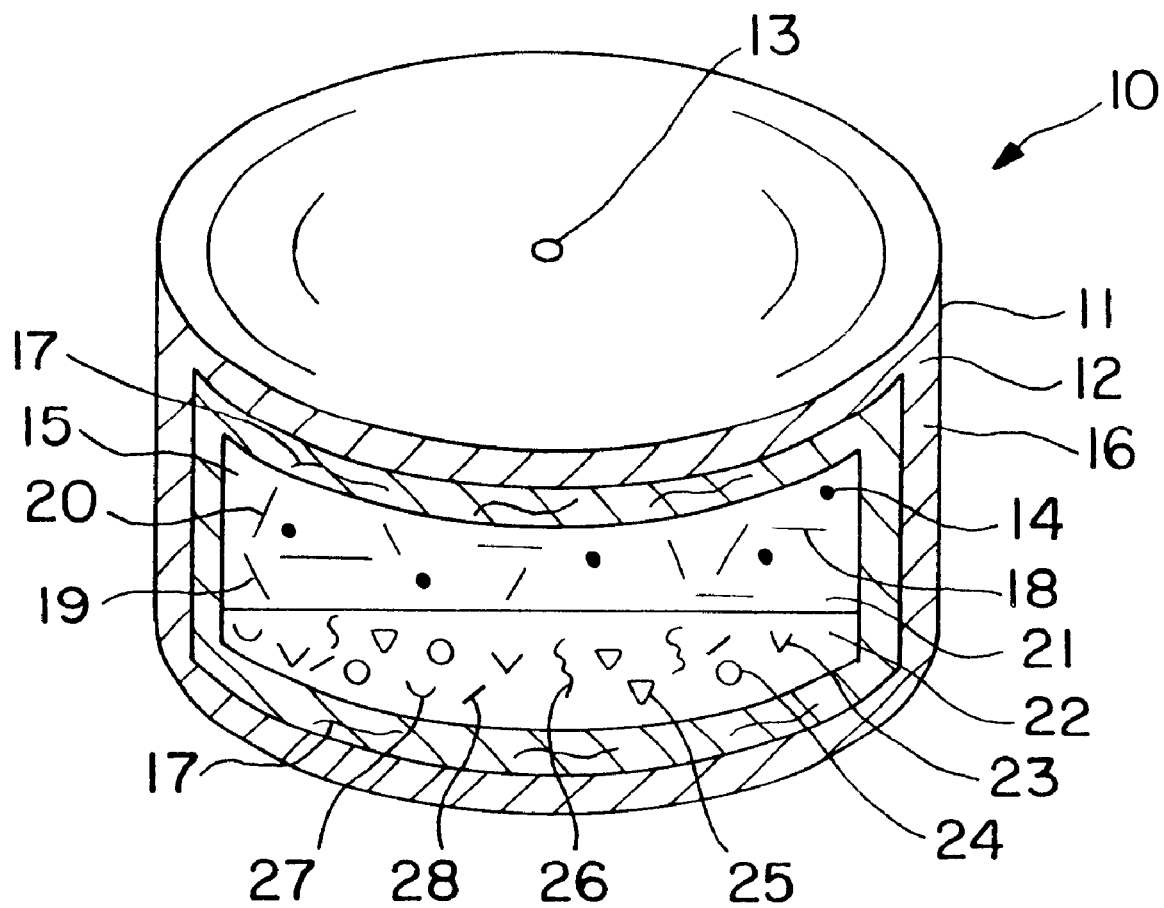
FIG. 3, is an opened view of drawing FIG. 1, illustrating a dosage form comprising a drug composition and a separate, but initially contacting push-displacement composition comprising means for pushing the drug composition from the dosage form.

Dosage form 10 as seen in drawing FIGS. 1 to 3, are useful for establishing therapeutic drug levels in the blood, including the plasma, for therapy. Dosage form 10, as seen in the accompanying figures, embraces the shape of a dosage tablet, and it can embrace the shape of a caplet, or a buccal, or a sublingual dosage form. The sustained-release dosage form of this invention provides extended-continuous delivery greater than conventional, noncontrolled tablets, or noncontrolled-nonsustained release tablets and/or capsules that exhibit a dose-dumping of their drug.

Dosage form 10 of drawing FIG. 2, comprises exterior, or second coat 12 that surrounds compartment 15. Second coat 12 comprises totally, or in at least a part a semipermeable composition. The semipermeable composition is permeable to the passage of an aqueous or an aqueous-biological fluid present in the gastrointestinal tract, and second coat 12 is impermeable to the passage of drug 14. Second coat 12 is nontoxic, and it maintains its physical and chemical integrity during the dispensing time of drug 14. The phrase, maintains its physical and chemical integrity means coat 12 does not lose its structure, and it does not undergo a chemical change during the dispensing of drug 14.

Coat 12 comprises a composition that does not adversely affect an animal, a human, or components of the dosage form. Compositions for forming coat 12 are, in one embodiments, comprised a member selected from the group consisting a cellulose ester polymer, a cellulose ether polymer and a cellulose ester-ether polymer. These cellulosic polymers have a degree of substitution, DS, on the anhydroglucose unit, from greater than 0 up to 3 inclusive. By "degree of substitution" is meant the average number of hydroxyl groups originally present on the anhydroglucose unit comprising the cellulose polymer that are replaced by a substituting group. Representative coat 12 polymers comprise a member selected from the group consisting of cellulose acylate, cellulose diacylate, cellulose triacylate, cellulose acetate, cellulose diacetate, cellulose triacetate, mono-, di- and tricellulose alkanylates, mono-, and di- and tricellulose alkinylates. Exemplary polymers include cellulose acetate having a DS of up to 1 and an acetyl content of up to 31%; cellulose acetate having a DS of 1 to 2 and any acetyl content of 21 to 35%; cellulose acetate having a DS of 2 to 3 and an acetyl content of 35 to 44.8%; and the like. More specific cellulosic polymers comprise cellulose propionate having a DS of 1.8, a propyl content of 39.2 to 45% and a hydroxyl content of 2.8 to 5.4; cellulose acetate butyrate having a DS of 1.8, an acetyl content of 13 to 15% and a butyryl content of 34 to 39%; cellulose acetate butyrate having a acetyl content of 2 to 29%, a butyryl content of 17% to 53% and a hydroxyl content of 0.5 to 4.7; cellulose triacylates having a DS of 2.9 to 3, such as cellulose trivalerate, cellulose trilaurate, cellulose tripalmitate, cellulose trisuccinate and cellulose trioctanoate; celluloses diacylate having a DS of 2.2 to 2.6, such as cellulose disuccinate, cellulose dipalminate, cellulose dioctanoate, cellulose dipentanoate, co-esters of cellulose, such as cellulose acetate butyrate, and cellulose acetate propionate.

Additional semipermeable polymers comprise acetaldehyde dimethylcellulose acetate; cellulose acetate ethylcarbamate; cellulose acetate methylcarbamate; cellulose diacetate propylcarbamate; cellulose acetate diethylaminoacetate; semipermeable polyamide; semipermeable polyurethane; semipermeable sulfonated polystyrene; semipermeable crosslinked selective polymer formed by the coprecipitation of a polyanion and polycation, as disclosed in U.S. Pat. Nos. 3,173,876; 3,276,586; 3,541,005; 3,541,006 and 3,546,876; semipermeable polymers as disclosed by Loeb and Sourirajan in U.S. Pat. No. 3,133,132; semipermeable, lightly crosslinked polystyrenes; semipermeable crosslinked poly(sodium styrene sulfonate); semipermeable cross-linked poly(vinylbenzyltrimethyl ammonium chloride); and semipermeable polymers possessing a fluid permeability in the range of $2.5 \times 10^{-8}$ to $5 \times 10^{-2}$ (cm$^2$/hr·atm), expressed per atmosphere of hydrostatic or osmotic pressure difference across the semipermeable wall. The polymers are known to the polymer art in U.S. Pat. Nos. 3,845,770; 3,916,899 and 4,160,020; and in *Handbook of Common Polymers*, by Scott, J. R. and Roff, W. J., 1971, CRC Press, Cleveland, Ohio. Second coat 12, in a present manufacture can be coated from a single solvent system, such as acetone.

Dosage form 10 comprises an interior or a first coat 16. The first coat 16 faces compartment 15, and second coat 12. Second coat 12 comprises a surface that faces the environment of use. First coat 16 comprises ethylcellulose, one hundred weight percent, (100 wt %), or in another manufacture a composition comprising a blend of 50 to 99 wt % ethylcellulose and 1 to 50 wt % hydroxypropylcellulose with the total weight of the compositional blend equal to 100 wt %. The first coat and the second coat are coated in a laminated arrangement free of heat and nonannealed to preserve the integrity and the properties of each coat. The ethylcellulose used for the first coat is nontoxic, insoluble in water, insoluble in gastrointestinal fluid, and soluble in ethyl alcohol, and in a solvent system comprising ethyl alcohol and water. The ethylcellulose used for the present purpose comprises a 20 to 60 weight percent ethoxy content, a viscosity 4 to 200 centipose or higher, and a 5,000 to 1,250,000 weight-average molecular weight. The hydroxypropylcellulose homogenously blended with the ethylcellulose is identified by a wave 17 in first coat 16. The hydroxypropylcellulose 17 comprises a 7,500 to 1,500,000 weight average molecular weight, and is soluble in water below 40° C. and in ethyl alcohol.

First coat 16 comprising hydroxypropylcellulose provides unexpected properties for this invention. For instance, ethylcellulose is hydrophobic and accordingly its fluid permeability is low which hinder sufficient water flux passing through the first coat to provide a wide-range of delivery rates. This invention, enhances the fluid permeability of the first coat by blending a hydrophilic fluid flux enhancer, which operates as a pore former in the first ethylcellulose coat. The hydrophilic enhancer increases the permeability of the ethylcellulose coat as it is dissolved and/or leached therefrom, to provide fluid-control pores. However, if the dosage form is manufactured with a single coat comprising a composition of ethylcellulose and hydroxypropylcellulose, as the pores are formed, the pores allow lipids, which are present in the gastrointestinal tract to sorb into this coat, which leads to an unaccepted change in this single coat. That is, the hydrophobic lipids cause the coat to become soft, placid and tearable as the lipid functions as a plasticizer within the ethylcellulose. The presence of the sorbed lipids cause the porous coat to become hydrophobic again, thereby reversing the desirable effects of the hydrophilic flux enhancer. The present invention unexpectedly discovered by providing a second coat comprising a cellulose acylate, the second coat excludes and prevents the lipids of the gastrointestinal tract from contacting and reaching the first coat. The first ethylcellulose-hydroxypropylcellulose-second cellulose acylate bilayer coat provides a wide range of low to high flux coats. Additionally, each coat can be coated from solvent removable by evaporation to provide reproducible coats.

In drawing FIG. 2, internal compartment 15 comprises a single homogenous composition. The compartment 15 comprises therapeutic agent 14, represented by dots. The term therapeutic agent as used herein included medicines or drugs, nutrients, vitamins, food supplements, and other beneficial agents that provide a therapeutic or a benefit to animals, including a warm-blooded animal, humans, farm animals, and zoo animals. Representative of therapeutic agent 14 comprise vancomycin, phentolamine, valoxifene, cyclosporin, lisinopril, ondansetron, fluvoxamine, captopril, enalapril, amisulpride, imipramine, carbamazepine, famciclovir, clomipramine, penciclovir, pergolide, mesalazine, enitabas, talviraline, clozapine, clopidogrel, nevirapine, zidoviudine, ganciclovir alendronic, imiquimod, naratriptan, sparflozacin, lamivudine, zidovudine, omeprazole, acyclovir, valaceclovir, oxcarbazepine, ganciclovir, amfebutamonc, cidofovir, doxazosin, ebastine, formoterol, moexipril, penciclovir, sertraline, spirapril, fenfluramine, dexfenfluramine, phentermine, fenphen, oxybutynin, felodipene, metoprolol, saquinavir, ritonavir, indinavir, and nelfinavir. The dose of drug 14 in compartment 15 is 0.5 mg to 750 mg.

Dosage form 10, in compartment 15 comprises a pharmaceutically acceptable hydrogel polymer 18, represented by level dashes. Representative polymer hydrogels comprise a maltodextrin polymer comprising the formula $(C_6H_{12}O_5)$ $\lambda.H_2O$, wherein $\lambda$ is 3 to 7,500, and the maltodextrin polymer comprises a 500 to 1,250,000 number-average molecular weight; a poly(alkylene oxide) represented by a poly(ethylene oxide) and a poly(propylene oxide) having a 50,000 to 750,000 weight-average molecular weight, and more specifically represented by a poly(ethylene oxide) of at least one of 100,000, 200,000, 300,000, or 400,000 weight-average molecular weights; an alkali carboxyalkylcellulose, wherein the alkali is sodium, or potassium, or calcium, the alkyl is methyl, ethyl, propyl, or butyl of 10,000 to 1,000,000 weight-average molecular weight; and a copolymer of ethylene-acrylic acid, including methacrylic and ethacrylic acid of 10,000 to 500,000 number-average molecular weight. The therapeutic composition comprises 5 to 400 mg of a polymer hydrogel. The therapeutic composition can be manufactured into dosage form 10 and it can be used as the therapeutic composition for its therapeutic effect. The hydrogel polymer exhibits an osmotic pressure gradient across bilayer first coat and second coat thereby imbibing fluid into compartment 15 to form a solution or a suspension comprising drug 14 that is hydrodynamically and osmotically delivered from dosage form 10.

Dosage form 10 comprises a binder 19 represented by left-slanted dashes 19. The binder imparts cohesive qualities to the composition. Representative of materials for this invention useful as binders comprise a member selected from the group consisting of starch, gelatin, molasses, a vinyl polymer comprises a 5,000 to 350,000 viscosity-average molecular weight, represented by a member selected from the group consisting of poly-n-vinylamide, poly-n-vinylacetamide, poly(vinyl pyrrolidone), also known as poly-n-vinylpyrrolidone, poly-n-vinylcaprolactone, poly-n-vinyl-5-methyl-2-pyrrolidone, and poly-n-vinylpyrrolidone copolymers with a member selected from the group consisting of vinyl acetate, vinyl alcohol, vinyl chloride, vinyl fluoride, vinyl butyrate, vinyl laureate, and vinyl stearate, methylcellulose, hydroxypropylcellulose, hydroxypropylmethylcellulose, and mixtures of binders. The binders can be used as a solution, or in a dry form to prepare the therapeutic composition. The therapeutic composition comprises 0 to 100 mg of a binder, and in the present manufacture from 0.01 to 25 mg of the binder.

Dosage form 10 comprises a lubricant 20 represented by right-slanted dashes 20. The lubricant is used during manufacture of the composition to prevent sticking to die walls or punch faces, generally to lessen adhesion. The lubricants are selected from the group consisting of sodium stearate, oleic acid, potassium oleate, caprylic acid, sodium stearyl fumarate, magnesium palmitate, calcium stearate, zinc stearate, magnesium stearate, magnesium oleate, calcium palmitate, sodium suberate, potassium laureate, stearic acid, salts of fatty acids, salts of alicyclic acids, salts of aromatic acids, oleic acid, palmitic acid, a mixture of a salt of a fatty, alicyclic or aromatic acid, an a mixture of magnesium stearate and stearic acid. The amount of lubricant in the therapeutic composition is 0.01 to 20 mg.

Drawing FIG. 3 depicts dosage form 10 in opened section illustrating internal compartment 15. Internal compartment 15 comprises the therapeutic composition containing drug 14, as described in detail in drawing FIG. 2. The therapeutic composition of drawing FIG. 2 is identified further in drawing FIG. 3 as drug layer 21. Drug layer 21 comprises the ingredients described in drawing FIG. 2 and the details previously disclosed are included in this description of drawing FIG. 3. Drug layer 21 in drawing FIG. 3 initially is in contact with push layer 22.

In drawing FIG. 3, push layer 22 comprises 10 mg to 400 mg of an expandable osmopolymer 23 represented by "v". The osmopolymer 23 in layer 22 possesses a higher molecular weight than the hydrogel polymer 18 in the drug composition. The osmopolymer 23 comprises a member selected from the group consisting of a polyalkylene oxide and a carboxyalkylcellulose. The polyalkylene oxide possesses a 1,000,000 to 10,000,000 weight-average molecular weight. Representative of polyalkylene oxide include a member selected from the group consisting of polymethylene oxide, polyethylene oxide, polypropylene oxide, polyethylene oxide having a 1,000,000 molecular weight, polyethylene oxide possessing a 2,000,000 molecular weight, polyethylene oxide comprising a 3,000,000 to 5,000,000 molecular weight, polyethylene oxide comprising a 7,000,000 and 7,800,000 molecular weight, cross-linked polymethylene oxide possessing a 1,000,000 molecular weight, and polypropylene oxide of 1,200,000 molecular weight. Typical osmopolymer 22 carboxyalkylcellulose in the expandable layer comprises a 200,000 to 7,250,000 weight-average molecular weight. Representative carboxyalkycellulose comprises a member selected from the group consisting of alkali carboxyalkylcellulose, sodium carboxymethylcellulose, calcium carboxymethylcellulose, potassium carboxymethyl-cellulose, sodium carboxyethylcellulose, lithium carboxyalkylhydroxy-alkylcellulose, sodium carboxyethy-cellulose, carboxyalkylhydroxy-alkylcellulose, carboxymethylhydroxyethylcellulose, carboxyethylhydroxy-ethylcellulose and carboxymethylhydroxypropylcellulose. The osmopolymers used for the push-expandable layer exhibit an osmotic pressure gradient across semipermeable coat 12. The omsopolymers imbibe fluid into dosage form 10, thereby swelling, expanding as a hydrogel or osmogel whereby, they push the drug from the osmotic dosage form.

Push layer 22 comprises 0 to 75 mg, and presently 0.5 to 75 mg of an osmotically effective compound 24, represented by circles. The osmotically effective compounds are known also as osmagents and as osmotically effective solutes. They imbibe an environmental fluid, for example, from the gastrointestinal tract, into dosage form 10 for contributing to the delivery kinetics of push layer 21. Representative of osmotically active compounds comprise a member selected from the group consisting of osmotic salts, such as sodium chloride, potassium chloride, magnesium sulfate, lithium phosphate, lithium chloride, sodium phosphate, potassium sulfate, sodium sulfate, potassium phosphate, osmotic carbohydrates; glucose, fructose and maltose, urea, tartaric acid, potassium acid phosphate, citric acid, and a mixture of sodium chloride and urea.

Push layer 22 comprises 0 to 75 mg of a suspending agent hydroxypropylalkyl-cellulose, represented by clear triangles 25. The hydroxypropylalkylcellulose comprises an alkyl of 1 to 7 carbons, straight or branched, with the hydroxypropylalkylcellulose possessing a 9,000 to 450,000 number-average molecular weight. The hydroxypropylalkylcellulose is represented by a member selected from the group consisting of hydroxypropylmethylcellulose, hydroxypropylethylcellulose, hydroxypropylisopropylcellulose, hydroxypropylbutylcellulose and hydroxypropylpentylcellulose. Push layer 22 optionally comprises a hydroxyalkylcellulose, also represented by triangles 25. The hydroxyalkylcellulose viscosity-increasing agent comprises a member selected from the group consisting of hydroxymethylcellulose, hydroxyethylcellulose, hydroxypropylcellulose and hydroxybutylcellulose comprising a 7,500 to 150,000 viscosity-average molecular weight. The amount of hydroxyalkycellulose is 0.00 to 40 mg.

Push layer 22 comprises 0 to 5 mg of a nontoxic colorant or dye 26 identified by vertical wavy lines. The colorant 26 makes the dosage form more esthetic in appearance, and it serves to identify the dosage form during manufacture and during therapy. The colorants include Food and Drug Administrations Colorant (FD&C), such as FD&C No. 1 blue dye, FD&C No. 4 red dye, FD&C yellow No. 5, FD&C yellow No. 6, FD&C blue No. 2, FD&C green No. 3, FD&C cranberry red No. 40, red ferric oxide, yellow ferric oxide, black ferric oxide, titanium dioxide, carbon black, indigo, and Opadry® comprising polymers, polysaccharides, cellulose, starch and dye commercially available from Colorcon, West Point, Pa.

A lubricant 27, identified by half circles, is formulated into push-expandable layer 22. Typical lubricants comprise a member selected from the group consisting of sodium stearate, potassium stearate, magnesium stearate, stearic acid, calcium stearate, sodium oleate, calcium palmitate, sodium laurate, sodium ricinoleate and potassium linoleate. The amount of lubricant is 0.01 to 10 mg.

An antioxidant 28, represented by slanted dashes, is present in push-expandable formulation 22 to inhibit the oxidation of ingredients comprising expandable formulation 22. Expandable formulation 22 comprises 0.00 to 5 mg of an antioxidant. Representative antioxidants comprise a member selected from the group consisting of ascorbic acid, ascorbyl palmitate, butylated hydroxyanisole, a mixture of 2 and 3 tertiary-butyl-4-hydroxyanisole, butylated hydroxytoluene, sodium isoascorbate, dihydroguaretic acid, potassium sorbate, sodium bisulfate, sodium metabisulfate, sorbic acid, potassium ascorbate, vitamin E, 4-chloro-2,6-ditertiary butylphenol, alpha-tocopherol, and propylgallate.

Dosage form 10, comprises another manufacture provided by the invention. Dosage form 10 comprises an overcoat not shown on the outer surface of the wall of dosage form 10. The overcoat is a therapeutic composition comprising 0.5 to 75 mg of drug and 0.5 to 275 mg of a pharmaceutically acceptable carrier selected from the group consisting of alkylcellulose, hydroxyalkylcellulose and hydroxypropylalkylcellulose. The overcoat is represented by methylcellulose, hydroxyethylcellulose, hydroxybutylcellulose, hydroxypropylcellulose, hydroxypropylmethylcellulose, hydroxypropylethylcellulose and hydroxypropylbutylcellulose. The overcoat is formulated with 0–50 weight percent of a plasticizer, opacificer, colorant, and antitact agents. The overcoat provides therapy immediately as the overcoat dissolves or undergoes dissolution in the presence of gastrointestinal fluid and concurrently therewith delivers the drug into the gastrointestinal tract for immediate drug therapy.

Dosage form 10, manufactured as an osmotically controlled-release dosage form, comprises at least one passageway 13. The phrase "controlled-release" as used herein indicates that control is exercised over both the duration and the profile of the drug release pattern. The expression "passageway" as used for the purpose of this invention, includes aperture, orifice, bore, pore, porous element through which drug 14 can be pumped, diffuse or migrate through a fiber, capillary tube, porous overlay, porous insert, microporous member, and porous composition. The passageway 13 includes also a compound that erodes or is leached from wall 12 in the fluid environment of use to produce at least one passageway. Representative compounds for forming a passageway include erodible poly(glycolic) acid, or poly(lactic) acid in the wall; a gelatinous filament; a water-removable poly(vinyl alcohol); leachable compounds such as fluid-removable pore-forming polysaccharides, acids, salts or oxides. A passageway can be formed by leaching a compound from wall 12, such as sorbitol, sucrose, lactose, maltose or fructose, to form a controlled-release dimensional pore-passageway. The passageway can have any shape, such as round, triangular, square and elliptical, for assisting in the controlled-metered release of drug 14 from the dosage form. The dosage form can be manufactured with one or more passageways in spaced-apart relation on one or more surfaces of the dosage form. A passageway and equipment for forming a passageway are disclosed in U.S. Pat. Nos. 3,845,770 and 3,916,899 by Theeuwes and Higuchi; in U.S. Pat. No. 4,063,064 by Saunders et al.; and in U.S. Pat. No. 4,088,864 by Theeuwes et al. Passageways comprising controlled-release dimensions sized, shaped and adapted as a releasing-pore formed by aqueous leaching to provide a releasing-pore of a controlled-release rate are disclosed in U.S. Pat. Nos. 4,200,098 and 4,285,987 by Ayer and Theeuwes.

DESCRIPTION FOR MANUFACTURING THE COMPOSITION AND DOSAGE FORM OF THE INVENTION

The first coat and the second coat of the dosage form can be formed by using the air suspension procedure. This procedure consists in suspending and tumbling the coat forming composition or the layer in a current of air and coat forming composition until a coat is applied to the drug forming compartment. The air suspension procedure is well suited for independently forming a coat. The air suspension procedure is described in U.S. Pat. No. 2,799,241; *J. Am. Pharm. Assoc.*, Vol. 48, pp. 451–454 (1959); and ibid., Vol. 49, pp. 82–84 (1960). The coat can be formed with a coat forming composition in a Wurster® air suspension coater using an organic solvent, such as acetone-water cosolvent 90:10 (wt;wt) with 2.5 wt % to 7 wt % polymer solids, for the second coat. The first coat can be formed in a like process using the solvent ethanol. An Aeromatic® air suspension coater can be used for applying both the first and second coats in successive application.

Other forming techniques, such as pan coating, can be used for providing the dosage form. In the pan coating system coat-forming compositions are deposited by successive spraying of the composition or the bilayered coat-arrangement, accompanied by tumbling in a rotating pan. A larger volume of cosolvent can be used to reduce the concentration of polymer solids to produce a thinner coat. Finally, the coat of the coated compartments are laser or mechanically drilled, and then dried in a forced air or humidity oven for 1 to 3 days or longer to free the solvent. Generally, the coats formed by these techniques have a thickness of 2 to 20 mils (0.051 to 0.510 mm) with a preferred thickness of 2 to 6 mils (0.051 to 0.150 mm).

The dosage form of the invention in another embodiment is manufactured by standard manufacturing techniques. For example, in one manufacture the beneficial drug and other ingredients comprising a therapeutic composition or comprising the first layer facing the exit means are blended, or the ingredients are blended then pressed, into a solid layer. The drug and other ingredients can be blended with a solvent and formed into a solid or semisolid formed by conventional methods such as ball-milling, calendaring, stirring or roll-milling and then pressed into a selected shape. The drug layer posses dimensions that correspond to the internal dimensions of the area the drug layer is to occupy in the dosage form. Next, the drug layer is placed in contact with the push-displacement layer. The layering of the drug layer and the push-displacement layer can be fabricated by conventional press-layering techniques. The bilayers possess dimensions corresponding to the dimensions of the internal compartment of the dosage form. Finally, the two-layer compartment forming members are surrounded and coated with an inner and outer coats. A passageway is laser drilled or mechanically drilled through the coats to contact the drug layer, with the dosage form optically oriented automatically by the laser equipment for forming the passageway on the preselected drug surface.

In another manufacture, the dosage form is manufactured by the wet granulation technique. In the wet granulation technique the drug and the ingredients comprising the first layer are blended using a solvent, such as isopropyl alcohol as the granulation fluid. Other granulating fluid, such as water, or denatured alcohol 100% can be used for this purpose. The ingredients forming the first layer are individually passed through a 40 mesh screen and then thoroughly blended in a mixer. Next, other ingredients comprising the first layer are dissolved in a portion of the granulation fluid, such as the solvent described above. Then, the latter prepared wet blend is slowly added to the drug blend with continual mixing in the blender. The granulating fluid is added until a wet blend mass is produced, which wet mass is then forced through a 20 mesh screen onto over trays. The blend is dried for 18 to 24 hours at 25° C. to 40° C. The dry granules are then screened with a 16 mesh screen. Next, a lubricant is passed through a 60 mesh screen and added to the dry screened granule blend. The granulation is put into milling jars and mixed on a jar mill for 2 to 10 minutes. The first and second layered compositions are pressed into a layered tablet, for example, in a Manesty® layer press.

Another manufacturing process that can be used for providing the drug and push-displacement compositions comprise blending their powdered ingredients in a fluid bed granulator. After the powdered ingredients are dry blended in the granulator, a granulating fluid, for example, poly (vinylpyrrolidone) in a solvent, such as in water, is sprayed onto the respective powders. The coated powders are then dried in a granulator. This process coats the ingredients present therein while spraying the granulating fluid. After the granules are dried, a lubricant, such as stearic acid or magnesium stearate, is blended as above into the mixture. The granules are then pressed in the manner described above. In another embodiment, when the fluid in granulating process is used to manufacture the push-displacement layer, an antioxidant present in the polyalkylene oxide can be removed during the processing step. If antioxidant is desired, it can be added to the push-displacement layer, and this can be accomplished during the fluid bed granulation described above.

The dosage form of this invention is manufactured in another embodiment by mixing a drug with composition-forming ingredients and pressing the composition into a solid layer possessing dimensions that correspond to the internal dimensions of the compartment space adjacent to a passageway. In another embodiment, the drug and other drug composition forming ingredients and a solvent are mixed into a solid, or semi-solid, by conventional methods such as ball-milling, calendaring, stirring, or roll-milling, and then pressed into a preselected, layer-forming shape.

In the general manufactures as presented herein, the manufacture comprising a drug and compositional forming ingredients are placed in contact with the push-displacement layer, and the drug layer and the push layers are surrounded then with the bilayered coats. The layering of the drug composition and the push-displacement composition can be accomplished by using a conventional two-layer tablet press technique. The coats can be applied by molding, spraying or dipping the pressed shapes into coat-forming materials. Another technique that can be used for applying the coat is the air-suspension coating procedure. This procedure consists in suspending and tumbling the two layers in a current of air until the coat forming composition are applied separately to the compartment layers. Manufacturing procedures are described in *Modern Plastics Encyclopedia*, Vol. 46, pp. 62–70 (1969); and in *Pharmaceutical Sciences*, by Remington, 14th ed., pp. 1626–1680 (1970) published by Mack Publishing Co., Easton, Pa. The dosage form can be manufactured by following the teaching the U.S. Pat. Nos. 4,327,725; 4,612,008; 4,783,337; 4,863,456; and 4,902,514.

DETAILED DISCLOSURE OF EXAMPLES

The following examples are merely illustrative of the present invention and they should not be considered as limiting the scope of the invention in any way, as these examples and other equivalents thereof will become apparent to those versed in the art in the light of the present disclosure and the accompanying claims.

Example 1

The therapeutic dosage form provided by the invention is prepared as follows: first, 2.4 g of oxybutynin hydrochloride, 42.6 of mannitol, and 194.8 g of polyethylene oxide of 100,000 weight-average molecular weight are dry blended for 10 minutes in a 200 ml beaker, with mixing for 10 minutes with a stainless steel spatula. Next, the dry blend drug composition is blended with 200 mg of magnesium stearate and the blended ingredients thoroughly blended to produce a homogenous drug composition. Next, the dry blend drug composition is compressed into a single layer tablet. Then, 150 mg of the drug composition is compressed under a pressure head of two-tons into a 9/32 inch (7.14 mm) diameter standard round tablet to provide the composition comprising the drug and the polyethylene oxide.

Next, the tablets are transferred to a tablet coating machine, where they are spray coated first with a solution of ethylcellulose comprising a 158,000 weight-average molecular weight and hydroxypropylcellulose comprising a number-average molecular weight of 85,000 in a solvent comprising ethanol and water. The percent ratio of ethylcellulose to hydroxypropylcellulose is 55 to 45, respectively. The coating solution is sprayed around the tablets to apply the first coat to a thickness of 5 mils (0.127 mm). Next, the tablets are coated with a 2 mil second coat comprising cellulose acetate comprising an acetyl content of 38.5% and a 40,000 weight-average molecular weight and polyethylene glycol of 400 molecular weight dissolved in acetone, to form the second coat. The present ratio of cellulose acetate to polyethylene glycol is 70 to 30, respectively. The dual coated dosage forms are air dried at 25° C. and a passageway is drilled through the dual coats to connect the drug composition with the exterior of the dosage forms.

Example 2

An osmotic dosage form with a second bioprotective coat which delivers 75 mg the anti-arrhythmic drug, encainide hydrochloride, at controlled rate was fabricated as follows: 500 grams of the drug, 233.8 grams of polyethylene oxide of molecular weight 200,000 grams per mole, 233.8 grams of polyethylene oxide of molecular weight 300,000 grams per mole, and 30 grams of hydroxypropyl methyl cellulose having a methoxyl content of 29 weight percent, a hydroxypropyl content of 10 weight percent, and a molecular weight of 11,300 grams per mole, were passed through a mesh having 40 wires per inch. The dried powders were tumble mixed for 5 minutes. To the dry mix was added slowly with stirring in a planetary mixer anhydrous ethyl alcohol until a damp mass was formed. The damp mass was then passed through a mesh having 20 wires per inch, producing granules which were air dried overnight at ambient conditions. After drying, the granules were passed again through the 20 mesh sieve. Then, 2.5 grams of magnesium stearate, previously passed through a mesh having 60 wires per inch, was tumble mixed into the granules for two minutes in a V-blender. This produced the finished drug layer granulation designated as drug layer 21.

Next, 687.5 grams of polyethylene oxide of molecular weight 7 million grams per mole, 200 grams of sodium chloride, 50 grams of hydroxypropyl methylcellulose as used to formulate the drug layer, 50 grams of cross-linked polyacrylic acid and 10 grams of ferric oxide, were passed through a 40 mesh sieve and dry mixed for five minutes. The resulting dry mix was wetted with anhydrous ethyl alcohol and formed into granules. Next, 2.5 grams of magnesium stearate sized 60 mesh was finally tumbled into the mixture. This procedure produced the finished push layer identified as layer 22.

Then, tablet cores of the dosage form were made by feeding each of the compositions separately to a bi-layer tablet press fitted with standard bi-concave 11/32 inch round tablet tooling die. The granulations were fed into the machine in individual hoppers. The drug layer composition was fed first and was lightly pretamped to form a lightly compressed mass weighing 165 mg per station. Push layer composition weighing 80 mg was then compressed onto the push layer composition with a final compression force of about 2 tons, thereby forming the bilayered tablet. Each core contained a unit dose of 75 mg of encainide hydrochloride.

Next, a batch of these bilayer tablets was transferred to a tablet coating machine where they were spray coated with a solution consisting of 64 grams ethyl cellulose having a molecular weight of 220,000 grams per mole and an ethoxyl content of 48.0–49.5 weight percent, 18 grams of hydroxypropyl cellulose having a molecular weight of 60,000 grams per mole and molar substitution of three, and 18 grams of polyethylene glycol having a molecular weight of 3,350 grams per mole. This composition was dissolved in mixture of 2,400 grams of anhydrous ethanol and 120 grams of distilled water. The solution was sprayed in a current of warm, dry air until a dry coating weight of 37 milligrams was deposited onto each of the bilayer cores. This coating is designated as the first coat or the interior coat of the dosage form. Then, a delivery portal was laser drilled with a diameter of 0.635 mm in the center of the tablet on the drug layer side.

In operation, when the dosage form comprising the first coat were immersed in vitro in an aqueous environment thermostated to 37 degrees centigrade, water was imbibed by osmosis across the membrane into the bilayer tablet, causing the drug to be released from the deliver port at an average rate of 3.75 mg encainide hydrochloride per hour over a duration of 20 hours. Four systems from this batch were then administered to dogs. All of the first, unprotected coatings ruptured in vivo and disintegrated during transit through the gastrointestinal tract as evidenced by coating fragments which were recovered in the stools. Therefore, the release of drug in vivo was unpredictable and uncontrolled, from the single-coated dosage form.

Next, 500 grams of the dosage forms coated with first coat were overcoated with a thin, bioprotective coating, the second coat. The bioprotective coating was applied as follows: first, 9.6 grams of polyoxyethylene 20 sorbitan tristearate, Tween 65—also known as polysorbate 65 available from ICI Industries, Inc. Then, 86.4 grams of triacetin (Tween 65) was dispersed in 3040 ml of distilled water with heat and stirring. Then, 86.4 grams of triacetin was then dissolved in this mixture. Next, 64 grams of cellulose acetate having an acetyl content of 39.8 weight percent and a molecular weight of 40,000 grams per mole previously micronized with an air jet mill to a nominal particle size of 3–5 microns was dispersed into the mixture with stirring continuous. The batch of cores were placed in an fluidized bed coater and the aqueous dispersion was applied to the bed of tablets in a current of warm air until a coating weight of 20 mg was applied, or approximately 2 mils coating thickness. This coating was designated as the second or exterior coat. The dosage form as manufactured by this process is administrable to humans for controlled and extended therapy.

Example 3

The dosage form manufactured in Example 2 was manufactured in this example with all the procedures followed as set-forth previously. In this example, a final finish coat, is overcoated onto the second coat. The finish coat consists of hydroxypropylmethylcellulose having a hydroxypropyl content of 10 weight percent, a methoxyl content of 29 weight percent and a molecular weight of 11,900 grams per mole of applied from an aqueous solution until a 20 mg was applied, forming the final coat, final coat three. The resulting coated systems were then dried in a forced air oven at 50 degrees centigrade for three days. Four of these systems were drilled with a delivery port and then administered to dogs. The animals were checked periodically and the presence or absence of residual systems in the stools was monitored. The window of time which the dosage form had resided within the animal was identified. All four systems were recovered from the stools of the animals and residual drug content was analyzed by high pressure liquid chromatography. The measured results of an animal study wherein the dogs were administered dosage forms comprising the first coat and the second coat are presented in Table 1. Dosage forms with the longest transit times had delivered all of the drug and dosage forms with shorter transit times delivered less drug as reported in Table 1. Thus, rate-controlled delivery in vivo was imparted to the dosage form by the presence of the bioprotective coating consisting of coat 2 and coat 3.

The coats of this invention, have been unexpectedly found to work in concert to achieve what neither coat could achieve alone. When the dosage form is coated with a single first coat, without the second coat, or without both the second coat and the third coat, the first coat broke-up in vivo and the dosage form released prematurely the unit dose of drug. The dosage forms coated only with coat 3, lacks the needed mechanical integrity to survive the mechanical abuse encountered in the gastrointestinal tract. Dosage forms coated only with the second coat, or with the second coat and the third coat and not the first coat lack release rate control. The dosage forms coated with the first coat and the second coat, or coated with the first, second and third coats surprisingly demonstrate acceptable therapeutic delivery rate control in vivo.

TABLE 1

| Dosage Forms No. | Transit Time (hours) | Percent of Dose Delivered (%) |
| --- | --- | --- |
| 1 | 49.3–50.5 | 101 |
| 2 | 30.3–46.0 | 98.4 |
| 3 | 30.3–46.0 | 94.8 |
| 4 | 28.0–28.8 | 80.8 |

Example 4

An osmotic dosage form with a bioprotective second coat which delivers the nasal decongestant, pseudoephedrine hydrochloride, was fabricated as follows. First, 715.4 grams of the drug, 99.6 grams of sodium chloride, 30.0 grams of hydroxypropyl methylcellulose having a hydroxypropyl content of 8 weight percent, a methoxyl content of 22 weight percent, and a molecular weight of 132,500 grams per mole, 100.0 grams of microcrystalline cellulose and 50.0 grams of polyvinyl pyrrolidone of molecular weight 10,000 grams per mole were passed through a mesh with 40 wires per inch, then tumble mixed for 10 minutes. Then, anhydrous ethyl alcohol was added to the mixed powders with stirring until a uniform damp mass was formed. This mass was passed through a sieve with 20 wires per inch, forming granules which were dried in forced air at 50 degrees centigrade for 24 hours. The dried granules were passed again through the 20 mesh sieve. Then, 5 grams of magnesium stearate was passed through a sieve with 80 wires per inch and then tumble mixed into the granules for 2 minutes. The resulting granulation was fed to a tablet press fitted with ⅜ inch round standard concave punch tooling. The granulation was compressed at a pressure head of 2 tons forming tablets which weighed 252 mg. Each tablet, which is referred to as drug Layer 1, contained a unit dose of drug of 180 mg.

The resulting tablets were coated using the procedures described in Example 2 with 5 mils of a coat consisting of 66 parts ethyl cellulose having an ethoxyl content of 48.0–49.5 weight percent and a molecular weight of 220,000 grams per mole, 29 parts hydroxypropyl cellulose having a molar substitution of three and molecular weight 60,000 grams per mole, and 5 parts polyethylene glycol with molecular weight 3350 grams per mole. This coating was designated as the first or interior coat. Four deliver ports were drilled through coats. Each port had a diameter of 20 mils. Two ports were located near the center of both sides. When immersed in normal saline thermostated at 37 degrees centigrade, water was imbibed across the coat by osmosis and drug was dispensed through the delivery ports at controlled rates. During and after the release test, the coat maintained their mechanical integrity in vitro.

Four more drilled systems were then administered to dogs. All four of the dosage forms disintegrated during transit through the gastrointestinal tract as evidenced by the fact that only fragments of the coat were recovered in the stools of the animals. Thus, the delivery of drug from these dosage forms in the absence of a bioprotective coat was controlled in vitro, but the delivery in vivo was uncontrolled.

Then, some dosage forms from this batch coated with a first coat and made without delivery ports were overcoated with a bioprotective second coat. The procedures and compositions used to apply the bioprotective coat are those detailed in Example 2. The bioprotective second coating consisted of 2 mils of 40 parts micronized cellulose acetate, 44 parts of triacetin, 10 parts of polyethylene glycol having a molecular weight 400 grams per mole, and 6 parts of surfactant polysorbate 65. In this example, after the bioprotective coat is applied, four delivery ports are formed through the coats. The dosage form provide by this manufacture administers a drug at a controlled and extended time for an indicated therapy.

Example 5

The procedure of Example 4 is followed to provide dosage form comprising a third coat, that is overcoat onto the second coat. The third coat is 2 mils (0.05 mm) thick and it comprises 70 parts hydroxypropylmethyl-cellulose having a methoxyl content of 29 weight percent and a hydroxypropyl content of 10 weight percent and a molecular weight of 11,300 grams per mole, and 30 parts of polyethylene glycol having a molecular weight of 8,000 grams per mole. The dosage forms were drilled with four delivery ports. When immersed into normal saline thermostated at 37° C., water was imbibed by osmosis. The dosage forms delivered drug at an average rate of 7 mg per hour for 24 hours.

Example 6

A series of six dosage forms coated with the first, second and third coats and comprising a drug delivery passageway were administered to dogs. All of the administered dosage forms were recovered in the stools of the dogs. The gastrointestinal transit time and the percent of dose of drug delivered are reported in accompanying Table 2. The data obtained from the study is consistent with and supports the unexpected results the delivery in vivo was well controlled by the dosage form. The results follow, for administering to the animals an osmotic dosage form comprising a nasal decongestant and a first coat and a second coat.

TABLE 2

| Dosage Forms No. | Transit Time (hours) | Percent of Dose Delivered (%) |
| --- | --- | --- |
| 5 | 54.8–70.0 | 98.4 |
| 6 | 54.8–70.0 | 99.9 |
| 7 | 26.8–27.0 | 87.5 |
| 8 | 30.5–45.8 | 94.4 |
| 9 | 50.8–51.8 | 97.0 |
| 10 | 30.5–45.8 | 93.9 |

Method of Practicing the Invention

The invention pertains additionally to the use of the therapeutic dosage form by providing a method for delivering a drug orally to a warm-blooded animal, including a human patient in need of therapy. The method comprises administering orally the therapeutic dosage form into the patient wherein the dosage form comprises a therapeutic composition surrounded by a first coat and a second coat, or a dosage form comprising a therapeutic composition and a push composition with both surrounded by a first coat and a second coat. The dosage form, in the gastrointestinal tract generates osmotic energy that cause the therapeutic composition to be administered through an exit port up to 40 hours to provide controlled and sustained therapy.

In summary, it will be appreciated that the present invention contributed to the art an unobvious dosage form that possesses practical utility, and can administer a drug at a dose-metered release rate per unit time. While the invention has been described and pointed out in detail with reference to operative embodiments thereof, it will be understood by those skilled in the art that various changes, modifications, substitution and omissions can be made without departing from the spirit of the invention. It is intended, therefore, that the invention embrace those equivalents within the scope of the claims which follow.

We claim:

1. An extended release dosage form comprising:
   a drug composition that comprises a drug and a pharmaceutically acceptable carrier, a first coat that surrounds the drug composition, wherein the first coat comprising ethyl cellulose and hydroxyalkycellulose;
   a second coat that surrounds the first coat, the second coat comprising a composition having at least one of a cellulose acylate, cellulose diacylate or cellulose triacylate wherein the composition is permeable to the passage of fluid and impermeable to the passage of drug; and
   an exit passageway in the first and second coats for releasing the drug from the dosage form over an extended time.

2. The extended release dosage form according to claim 1, wherein the first coat comprises 55 to 99 wt % of ethyl cellulose and 1 to 50 wt % of the hydroxyalkylcellulose.

3. The extended release dosage form according to claim 1, wherein the hydroxyalkylcellulose is hydroxypropylcellulose.

4. The extended release dosage form according to claim 1, wherein the pharmaceutically acceptable carrier is a hydrogel.

5. The extended release dosage form according to claim 1, wherein the dosage form comprises an expandable composition comprising a hydrogel.

6. The extended release dosage form according to claim 1, wherein the pharmaceutically acceptable carrier is a hydrogel.

7. The extended release dosage form according to claim 1, wherein the exit passageway is a pore.

8. The extended release dosage form according to claim 1, wherein the drug is oxybutynin.

9. The extended release dosage form according to claim 1, wherein the pharmaceutically acceptable carrier is poly (ethylene oxide) of 50,000 daltons to 750,000 daltons molecular weight.

10. The extended release dosage form according to claim 6, wherein the dosage form comprises an expandable composition comprising a hydrogel that possesses a higher molecular weight than the pharmaceutically acceptable carrier hydrogel.

11. The extended release dosage form according to claim 1, wherein the drug is selected from the group consisting of vancomycin, phentolamine, valoxifene, cyclosporin, lisinopril, ondansetron, fluvoxamine, captopril, enalapril, amisulpride, imipramine, carbamazepine, famciclovir, clomipramine, penciclovir, pergolide, mesalazine, enitabas, talviraline, clozapine, clopidogrel, nevirapine, zidoviudine, ganciclovir alendronic, imiquimod, naratriptan, sparflozacin, lamivudine, omeprazole, acyclovir, valaceclovir, oxcarbazepine, ganciclovir, amfebutamonc, cidofovir, doxazosin, ebastine, formoterol, moexipril, penciclovir, sertraline, spirapril, fenluramine, dexfenfluramine, phentermine, fenphen, oxybutynin, felodipene, metoprolol, saquinavir, ritonavir, indinavir, and neflinavir.

12. The extended release dosage form according to claim 1, wherein the drug is present in the extended release dosage form in an amount of 0.5 mg to 750 mg.

13. A method for providing controlled delivery of a drug to a mammal over an extended time period comprising:
   providing an extended release dosage form comprising a drug composition that comprises a drug and a pharmaceutically acceptable carrier, a first coat that surrounds the drug composition, wherein the first coat comprising ethyl cellulose and hydroxyalkycellulose, a second coat that surrounds the first coat, the second coat comprising a composition having at least one of a cellulose acylate, cellulose diacylate or cellulose triacylate wherein the composition is permeable to the passage of fluid and impermeable to the passage of drug, and an exit passageway in the first and second coats for releasing the drug from the dosage form over an extended time; and
   administering to the mammal the extended release dosage form.

* * * * *